United States Patent [19]

Miranda et al.

[11] Patent Number: 4,915,950
[45] Date of Patent: Apr. 10, 1990

[54] PRINTED TRANSDERMAL DRUG DELIVERY DEVICE

[75] Inventors: Jesus Miranda, Menlo Park; Gary W. Cleary, San Mateo, both of Calif.

[73] Assignee: Cygnus Research Corporation, Redwood City, Calif.

[21] Appl. No.: 215,074

[22] Filed: Jul. 5, 1988

Related U.S. Application Data

[63] Continuation-in-part of Ser. No. 155,327, Feb. 12, 1988, abandoned.

[51] Int. Cl.$^4$ ............................................. A61F 13/02
[52] U.S. Cl. .................................... 424/448; 424/447; 424/449
[58] Field of Search ........................ 424/448, 449, 447

[56] References Cited

U.S. PATENT DOCUMENTS

| | | | |
|---|---|---|---|
| 3,996,934 | 12/1976 | Zaffaroni | 128/268 |
| 4,460,372 | 7/1984 | Campbell et al. | |
| 4,552,872 | 12/1985 | Cooper et al. | |
| 4,557,934 | 12/1985 | Cooper | |
| 4,568,343 | 2/1986 | Leeper et al. | |
| 4,588,580 | 5/1986 | Gale et al. | 424/449 |
| 4,597,961 | 7/1986 | Etscorn | |
| 4,743,249 | 5/1988 | Loveland | 424/447 |
| 4,781,924 | 11/1988 | Lee et al. | 424/486 |

FOREIGN PATENT DOCUMENTS

| | | |
|---|---|---|
| 250125 | 12/1987 | European Pat. Off. |
| 267061 | 5/1988 | European Pat. Off. |
| WO88/01516 | 3/1988 | PCT Int'l Appl. |

*Primary Examiner*—Thurman K. Page
*Assistant Examiner*—P. L. Prater
*Attorney, Agent, or Firm*—Dianne E. Reed

[57] ABSTRACT

A method for making transdermal drug delivery devices is provided which includes: laminating an adsorbent source layer to a pressure-sensitive, pharmaceutically acceptable contact adhesive; depositing a drug in liquid form on one face of the source layer; laminating an anchor adhesive layer to the opposing face of the source layer; and applying a drug-impermeable backing layer to the anchor adhesive, which backing layer then defines the upper surface of the device. The invention also encompasses transdermal drug delivery devices having a source layer in contact with and contained between anchor and contact adhesive layers, with a backing layer adjacent the anchor adhesive defining the upper surface of the device.

12 Claims, 3 Drawing Sheets

PRINTED TRANSDERMAL DRUG DELIVERY DEVICE

CROSS-REFERENCE TO RELATED APPLICATION

This is a continuation-in-part of U.S. application Ser. No. 155,327, filed 12 Feb. 1988 now abandoned.

DESCRIPTION

1. Technical Field

This invention relates generally to transdermal drug delivery devices, and more particularly relates to such devices in which the drug is "printed", or deposited, on a central source layer during device fabrication. The invention thus encompasses a method for making transdermal drug delivery devices using a printing step to incorporate the drug into a source layer, and to drug delivery devices made using the novel method.

2. Background of the Invention

A variety of devices have been proposed or used for administering drugs transdermally. These devices are generally in the form of a bandage or skin patch that includes a reservoir that contains the drug and a pressure-sensitive adhesive component by which the device is attached to the skin. Depending upon the inherent permeability of the skin to a particular drug, the device may also include means for coadministering a percutaneous absorption enhancer or an element, such as a membrane interposed between the reservoir and the skin, that regulates the rate at which the drug or the percutaneous absorption enhancer is administered to the The commercially available techniques for manufacturing these devices involve conventional casting and laminating processes. Actual incorporation of the drug is typically effected by (1) admixture of the drug with a compatible solvent, (2) incorporation of the drug into the drug reservoir by immersion in the drug/solvent admixture, and (3) evaporation of the solvent. In practice, this method has proved to have several disadvantages.

First, for many drugs, the solvent selected is necessarily organic, rather than aqueous. As many organic solvents are flammable and/or toxic, an element of risk is thus introduced into device fabrication and use. Another shortcoming is that with volatile drugs or drugs that are sensitive to heat, evaporation of the solvent can either volatilize or degrade the drug. The present invention is addressed to these shortcomings, and provides a device fabrication process which eliminates the necessity for both organic solvents and high-temperature evaporation. The process minimizes drug degradation and loss to the environment, while eliminating the possibility of contamination with organic residues which may be harmful to the skin, e.g., as irritants, sensitizers, carcinogens, or the like.

Furthermore, conventional casting is done in solid sheets or stripes. When laminated and die cut out the remaining web is left unusable and is discarded. Highly expensive drugs are costly to discard, as dangerous or controlled narcotic drugs can be diverted for abuse or present other uncontrollable hazards. Printing a precise pattern will allow a drugless web remaining that is less costly, dangerous, and without the potential for abuse.

Because the fabrication process does not involve the use of high temperatures, it is also useful in incorporating volatile vehicles, excipients or enhancers into transdermal delivery devices. In addition, a device may be fabricated using the present process so as to contain a volatile fragrance. Such a device is designed to exude fragrance over a protracted, predetermined period of time.

DISCLOSURE OF THE INVENTION

One aspect of the invention is a method for making a transdermal delivery device, comprising:

(a) laminating an adsorbent source layer to a pressure-sensitive, pharmaceutically acceptable contact adhesive layer, the contact adhesive layer comprised of a material that is permeable to the drug and which defines a basal surface for adhesion to skin;

(b) depositing a drug in liquid form on one face of the adsorbent source layer;

(c) laminating an anchor adhesive layer to the opposing face of the source layer; and (d) applying a backing layer to the anchor adhesive layer which defines the upper surface of the device and is substantially impermeable to the drug.

Another aspect of the invention is a transdermal drug delivery device in the form of a laminated composite comprising:

(a) a backing layer that is substantially impermeable to the drug and which defines the upper surface of the device;

(b) an anchor adhesive layer adjacent the opposing face of the backing layer and laminated thereto;

(c) a layer of a pressure-sensitive, pharmaceutically acceptable contact adhesive layer, comprised of a material that is permeable to the drug, and which defines the basal surface of the device and contacts and adheres to the skin when the device is in use; and (d) an adsorbent source layer in contact with and contained between layers (b) and (c), wherein a drug becomes dispersed throughout said contact adhesive layer after equilibrium is reached.

In still another aspect of the invention, a method and device similar to the aforementioned are provided for the incorporation and release of fragrance. In such a case, the fragrance is initially deposited onto the source layer and then released over time through the adhesive and backing layers which are selected so as to be permeable to the fragrance.

A key advantage of the present invention is in the "printing" of the selected drug, drug-vehicle combination, or other material, in liquid form, on the adsorbent source layer. That is, the material is loaded into the device by substantially uniform deposition on the surface of the source layer. For many materials, this one-step deposition eliminates the need for organic solvents as well as the need for heat treatment.

After loading of the drug onto the source layer, the drug migrates into the underlying contact adhesive layer and, depending on the material selected for the anchor adhesive layer, into that layer as well. The release kinetics of the drug into the skin from the contact adhesive layer are determined by the degree of drug loading (which can be at, above, or below saturation in this system) and the diffusivity and solubility of the drug in the two adhesive layers. The source layer thus serves to initially retain the deposited drug which then migrates from the source layer into one or both adhesive layers.

MODES FOR CARRYING OUT THE INVENTION

1. Definitions:

By "printed" as used herein to describe the method of incorporating drug or other material into the source layer is meant a substantially uniform deposition of the drug, in liquid form, onto one surface of the source layer. As the source layer comprises a porous material, the drug is initially retained by that layer, i.e., prior to equilibration, and then diffuses into one or both of the adjacent layers. It will be appreciated by those skilled in the art that a variety of techniques may be used to effect substantially uniform deposition of material, e.g., Gravure-type printing, extrusion coating, screen coating, spraying, painting, or the like.

By a drug in "liquid form" as used herein is meant either a drug that is itself a liquid or a drug which is suspended, dissolved or dispersed in a selected solvent. Solvents may or may not be aqueous, depending on the particular drug used, and may include commonly used liquid vehicles and skin penetration enhancers. Preferred solvents are nonaqueous and selected so that they can be incorporated into the final system without adverse effect.

By "pharmaceutically acceptable" material as used herein is meant a material which does not interfere with the biological effectiveness of the drug administered and which is not for any reason biologically or otherwise undesirable.

By a "permeable" adhesive is meant a material in which the selected drug has at least moderate solubility and diffusivity, i.e., drug solubility on the order of 5 to 50 wt. %, preferably 10 to 30 wt. %, and diffusivity in the range of about $1 \times 10^{31\ 6}$ to about $b\ 1 \times 10^{-12}$ cm$^2$/sec.

By "substantially impermeable" as used herein to describe the backing layer is meant that an effective amount of the selected drug will be contained within the device without loss of any substantial amount through the backing layer. It should be noted that where the device is used for the release of fragrance, however, fragrance. In such an embodiment, the device thus allows for release of fragrance into the atmosphere.

Figure 1:
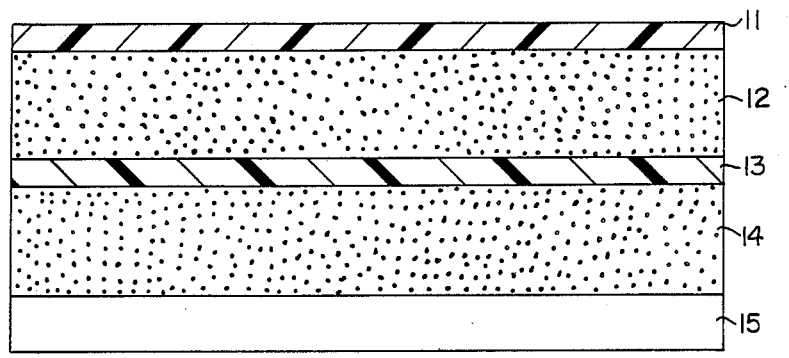
FIG. 1 shows a partly schematic, sectional view of a transdermal drug delivery device according to the invention.

2. Description of the Device:

Referring now to FIG. 1, the transdermal drug delivery device provided by the present method is shown generally at 10. The device is designed specifically for transdermal administration of a drug at controllable, therapeutically effective rates. The device 10 is in the form of a laminated composite that is adapted to be adhered to a predetermined area of unbroken skin or mucosal tissue. The individual layers of the device include an upper backing or "outer skin" layer 11, an anchor adhesive layer 12, a source layer 13 onto which the drug and/or vehicles are deposited initially, a contact adhesive 14 which is adapted to adhere to the skin or mucosa, and a release liner 15.

The backing layer 11 functions as the primary structural element of the device and provides the device with much of its flexibility, suitable drape, and, where necessary, depending upon the material incorporated into the device, occlusivity. In the preferred embodiment in which the device serves as a transdermal drug delivery system, the backing layer also serves as a protective covering to prevent loss of drug (and/or vehicle, solubilizer or permeation enhancer, if present) via transmission through the upper surface of the device. (In the alternative embodiment in which the device serves as a fragrance patch, as noted above, the backing layer will by contrast allow release of fragrance into the atmosphere.) Backing layer 11 may also be used to impart the device with a desirable or necessary degree of occlusivity which in turn causes the area of skin on which the device is placed to become hydrated. In such a case, a layer is selected that has a level of water vapor transmissibility that makes the device occlusive to the degree required to cause the area of skin to be hydrated. It is then preferable that the device provide at least about 90% hydration, more preferably at least about 95% hydration of the skin, as measured by a dielectric hydration probe available from Dr. Howard Maibach, U.C.S.F., San Francisco, Calif. Such occlusivity is desirable when drugs such as estradiol or other steroids are being administered. If the drug being administered is such that skin hydration is not necessary or desirable, it is preferable to use layers that provide a composite that is "breathable", i.e., transmits water vapor from the skin to the atmosphere. Such breathability contributes to the nonocclusive nature of the composite and lessens the likelihood that the area of skin on which the composite is worn will become highly hydrated and irritated.

Backing 11 is preferably made of a sheet or film of a preferably flexible elastomeric material that is substantially impermeable to the selected drug. The layer is preferably on the order of 0.0005" to 0.003" in thickness, and may or may not contain pigment. The layer is preferably of a material that permits the device to mimic the contours of the skin and be worn comfortably on areas of skin, such as at joints or other points of flexure, that are normally subjected to mechanical strain with little or no likelihood of the device disengaging from the skin due to differences in the flexibility or resiliency of the skin and the device. Examples of elastomeric polymers that are useful for making layer 11 are polyether block amide copolymers (e.g., PEBAX copolymers), polyethylene methyl methacrylate block copolymers (EMA) such as NUKRELL polymers, polyurethanes such as PELLATHANE or ESTANE polymers, silicone elastomers, polyester block copolymers that are composed of hard and soft segments (e.g., HYTREL polymers), rubber-based polyisobutylene, styrene, and styrene-butadiene and styrene-isoprene copolymers. Polymers that are flexible include polyethylene, polypropylene, polyesters, e.g., polyester terephthalate (PET), which may be in the form of films or laminates. The preferred polymer used for the backing will depend on the material or drug incorporated into the device and on the nature of any vehicles, solubilizers, or the like that are used.

Anchor adhesive layer 12 adheres to backing layer 11 and to source layer 13. The anchor adhesive is preferably but not necessarily of a material in which the selected drug or vehicle has moderate solubility and diffusivity. In such a case, after equilibration, the drug will have diffused not only into the contact adhesive layer 14, but also into the anchor adhesive. Diffusion into both adhesive layers is useful insofar as regulation of release kinetics is concerned. That is, by careful selection of the materials used for the anchor and contact adhesive layers, the distribution of drug throughout the entire system can be regulated. This is because the release kinetics of the drug from the device can be controlled by the diffusivity and solubility of the drug in both of the adhesive layers as well as in backing layer 11. When the drug is below saturation in all layers, the total drug loading can control the release kinetics.

Examples of suitable materials for anchor adhesive layer 12 include polyethylenes, polysiloxanes, polyisobutylenes, polyacrylates, polyurethanes, plasticized ethylene-vinyl acetate copolymers, low molecular weight polyether block amide copolymers (PEBAX copolymers), tacky rubbers such as polyisobutene, polystyrene-isoprene copolymers, polystyrene-butadiene copolymers, and mixtures thereof. The particular polymer(s) used for the anchor adhesive layer will depend on the drug, vehicle, enhancer, etc., selected. The thickness of the anchor adhesive layer may vary but is typically in the range of about 0.0005" to about 0.005".

In the case of a fragrance patch, the material serving as the anchor adhesive layer should, like the backing layer, be selected so as to be substantially permeable to the fragrance incorporated into the patch.

Source layer 13 is a thin, flexible layer of an adsorbent material which provides the surface on which the drug is printed or otherwise deposited. The source layer allows the liquid drug (together with vehicle, solubilizer or the like) to be printed on its surface as a result of having surface properties not found in either the contact or anchor adhesive layers. During fabrication, the drug is deposited in liquid form onto one face of this layer in a substantially uniform pattern. The drug must wet the surface in such a way that squeezing of liquid to the periphery of the device during lamination is substantially prevented. The material is selected so that the drug is adsorbed, rather than absorbed, by the layer, since the drug must be available to migrate into contact adhesive layer 14 and preferably into anchor adhesive layer 12 as well. The source layer is preferably of a non-woven fabric, e.g., polyester, polyethylene, polypropylene, polyamides, rayon or cotton, and a particularly preferred material for the source layer is a 100% non-woven polyester. Woven fabrics, however, can also be used if desired. The thickness of the source layer may vary, but is preferably in the range of about 0.001" to 0.010".

It should be pointed out that the source layer does not serve as a drug reservoir; drug is only transiently adsorbed by the source layer pending equilibration, i.e., migration into one or both of the adjacent adhesive layers.

Alternatively, the inner surface of either the anchor or contact adhesive layers may be treated and thus itself serve as the source layer for purposes of drug deposition. Still another alternative is to use a contact or adhesive layer that has a porous surface, enabling drug to be printed "into" the surface pores.

Contact adhesive layer 14, which plays the principal role in determining the rate at which drug is released from the device, is a pressure-sensitive skin contact adhesive comprised of a pharmaceutically acceptable material. Like source layer 13, it must be chemically and physically compatible with the drug and with any enhancer used. Further, the drug selected must have at least moderate solubility and diffusivity in this layer, since the drug must be able to readily migrate from source layer 13 into and through contact adhesive layer 14 and to the skin. The thickness of the contact adhesive layer is preferably in the range of about 0.0005" to about 0.005".

Suitable materials for contact adhesive layer 14 include those enumerated for anchor adhesive 12. It is possible (in some cases) to use materials for the contact adhesive layer that are relatively impermeable to the drug, e.g., where the diffusivity of the drug through skin is quite high. In the case of a fragrance patch, contact adhesive layer 14 may or may not be permeable to the fragrance. In any particular device fabricated according to the present process, the materials chosen for the contact and anchor adhesive layers may be the same or different.

Prior to use, device 10 includes a release liner 15. Just prior to use, this layer is removed from the device to expose contact adhesive layer 14. The release liner will normally be made from a drug/vehicle/enhancer impermeable material that is inherently "strippable" or rendered so by techniques such as silicone or fluorocarbon treatment.

Device 10 need not include a means for controlling the rate at which either the drug or the enhancer is administered to skin. Instead, the release kinetics of the drug from the bandage can be controlled by the materials selected for the anchor and contact adhesive layers and by the degree of drug loading. Either the contact adhesive layer or the source layer could be rate-controlling, depending on the drug and materials selected. Alternatively, drug and/or vehicle microencapsulated to provide controlled release could be deposited on the source layer prior to lamination, i.e., instead of deposition of drug in "liquid form" as previously defined. Typically, over the effective lifetime of the device, drug is presented to the skin at a rate in excess of the rate that the treated area of skin is able to absorb. It will be appreciated, however, that depending upon the particular drug (and enhancer when one is needed) that is being administered, that it may be necessary or desirable to include an element in the device that will control the release rate of the drug and/or the enhancer. Such elements are known in the art. The most common is a polymer membrane having appropriate drug/enhancer permeability properties interposed between the source layer and the contact adhesive layer.

The term "drug" as used to describe the principal active ingredient of the device intends a biologically active compound or mixture of compounds that has a therapeutic, prophylactic or other beneficial pharmacological and/or physiological effect on the wearer of the device. Examples of types of drugs that may be used in the inventive device are antiinflammatory drugs, analgesics, antiarthritic drugs, tranquilizers, narcotic antagonistis, antiparkinsonism agents, anticancer drugs, immunosuppression agents, antiviral agents, antibiotic agents, appetite suppressants, antiemetics, anticholinergics, antihistaminics, antimigraine agents, coronary, cerebral or peripheral vasodilators, anti-anginals, e.g., calcium channel blockers, hormonal agents, contraceptive agents, antithrombotic agents, diuretics, antihypertensive agents, cardiovascular drugs, chemical dependency drugs, and the like. The appropriate drugs of such types are capable of permeating through the skin either inherently or by virtue of treatment of the skin with a percutaneous absorption enhancer. Because the size of the device is limited for patient acceptance reasons, the preferred drugs are those which are effective at low concentration in the blood stream. Examples of specific drugs are steroids such as estradiol, progesterone, norethindrone, norethindrone acetate, levonorgestrel, ethynodiol diacetate, norgestamate, gestadene, desogestrel, 3-keto desogestrel, demegestone, promegestrone, testosterone, hydrocortisone, and their esters; nitro compounds such as amyl nitrate, nitroglycerine and isosorbide nitrates; amine compounds such as nicotine, chlorpheniramine, terfenadine and triprolidine; oxicam derivatives such as piroxicam; mucopolysaccharidases such as thiomucase; opioids such as buprenorphine, fentanyl and fentanyl derivatives or analogs, naloxone, codeine, dihydroergotamine, pizotiline, salbutamol and terbutaline; prostaglandins such as those in the PGA, PGB, PGE and PGF series, e.g., misoprostol and enprostil, omeprazole, imipramine; benzamides such as metoclopramine and scopolamine; peptides such as growth releasing factor, growth factors (EGF, TGF, PDGF and the like), and somatostatin; clonidine; dihydropyridines such as nifedipine, verapamil, diltiazem, ephedrine, propanolol, metoprolol and spironolactone; thiazides such as hydrochlorothiazide and flunarizine; sydononimines such as molsidomine; sulfated polysaccharides such as heparin fractions; and the salts of such compounds with pharmaceutically acceptable acids or bases, as the case may be. The loading of drug in the device will depend on the intended lifetime of the device and will usually be in the range of about 0.1% to 20% by weight.

It should be noted that the present method and device are suitable for use with volatile drugs and excipients, as no heat treatment step is involved or necessary. Thus, the present invention is useful with drugs such as nicotine, nitroglycerin, amyl nitrate, and scopolamine. The present device is also useful with drugs such as fentanyl, which will typically be incorporated into the patch using nonaqueous, volatile vehicles and/or enhancers which, because they volatilize during heat treatment, have proven difficult to incorporate into a transdermal delivery device by conventional means.

Since the inherent permeability of the skin to some drugs, such as steroids, is too low to permit therapeutic levels of such drugs to pass through a reasonably sized area of unbroken skin, it is necessary to coadminister a percutaneous absorption enhancer with such drugs. Accordingly, in such a case, a percutaneous absorption enhancer will be present in the device along with the drug, i.e., will be initially deposited on source layer 13 together with the drug. In addition to affecting the permeability of the skin to the drug, the enhancer may also increase the diffusivity of the drug in the source layer and in the adhesive layers, thus increasing the permeability of the device as a whole to the drug. Any number of the many percutaneous absorption enhancers known in the art may be used in conjunction with the present invention. For examples of suitable enhancers, see U.S. Pat. Nos. 3,996,934; 4,460,372; 4,552,872; 4,557,934 and 4,568,343 and the patents referenced therein.

When the inventive device is used to administer drugs to which the permeability of the skin is inherently too low to allow passage of therapeutic amounts of drug, enhancers will be included in the device, "printed" onto the source layer along with the drug or incorporated into one or both of the adhesive layers. Correlatively, when the device is used to administer a drug to which the permeability of the skin is inherently sufficient to pass therapeutic amounts, it is not necessary to coadminister an enhancer. Thus, in general terms, the inclusion of an enhancer in the device is optional depending on the particular drug that is being administered.

Figure 2:
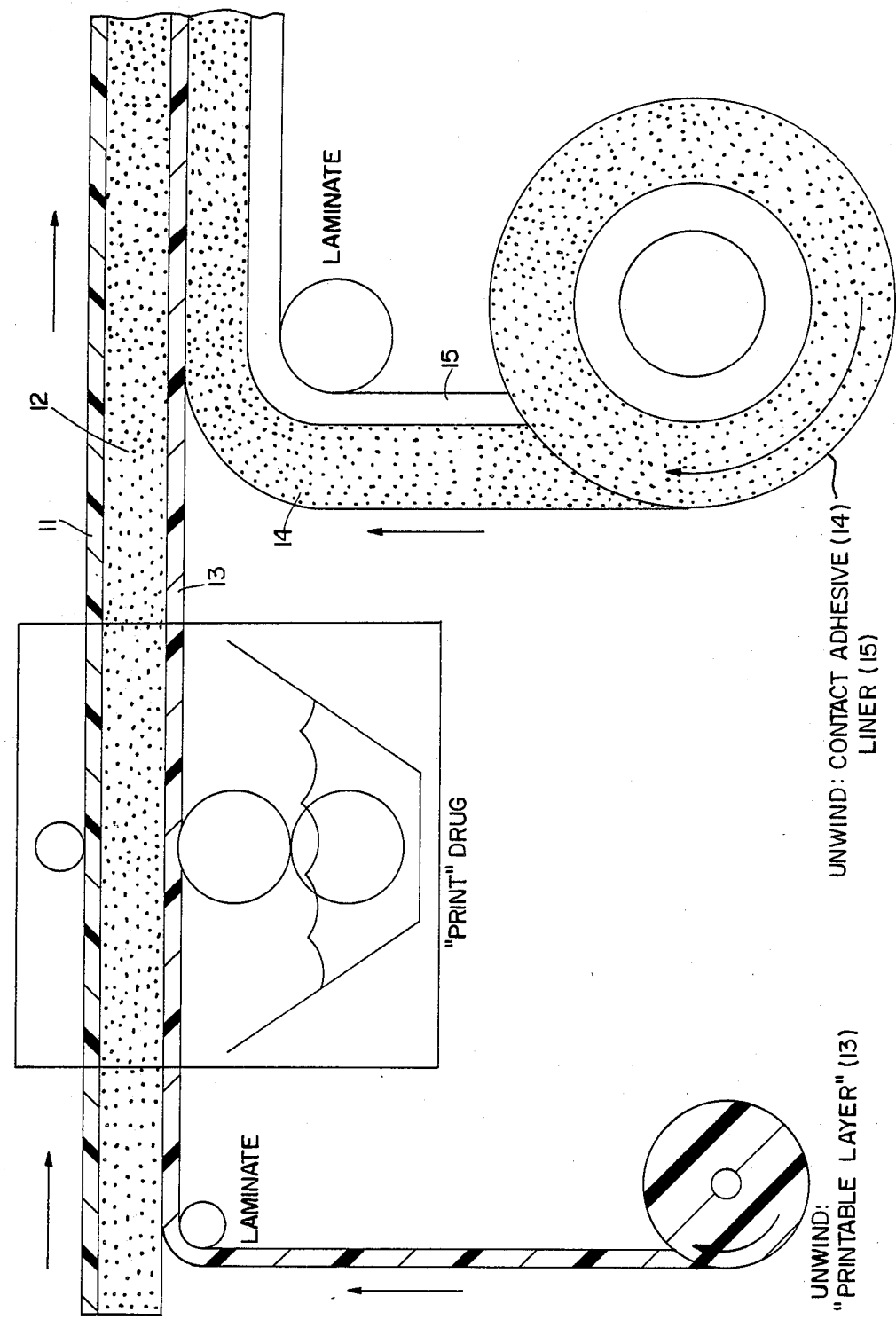
FIG. 2 shows an apparatus which may be used in fabricating a transdermal drug delivery device according to the method of the invention.

3. Fabrication:

The device of the present invention is readily manufactured as follows. As illustrated by FIG. 2, anchor adhesive 12 may be roll-coated onto a backing layer 11 of a commercially available film at a coating weight in the range of about 0.2 mg/cm$^2$ to 15 mg/cm$^2$, more preferably in the range of about 1 mg/cm$^2$ to 10mg/cm$^2$. Similarly, the pressure-sensitive skin contact adhesive 14 may be coated onto release liner 15 at a coating weight in the range of 0.2 mg/cm$^2$ to 15 mg/cm$^2$, more preferably 1 mg/cm$^2$ to 10 mg/cm$^2$. The source layer 13 is then deposited onto either contact adhesive layer 14 or onto anchor adhesive 12, preferably onto the contact adhesive. The selected drug in liquid form (optionally admixed with enhancer), is then printed onto the exposed surface of source layer 13 using conventional printing techniques. In an alternative embodiment of the invention, the drug is initially contained in one or both of the anchor and contact adhesive layers (e.g., by incorporation of the drug into the layers prior to lamination), and enhancer and/or vehicle is printed onto the source layer.

It is to be understood that while the invention has been described in conjunction with the preferred specific embodiment thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Figure 3:
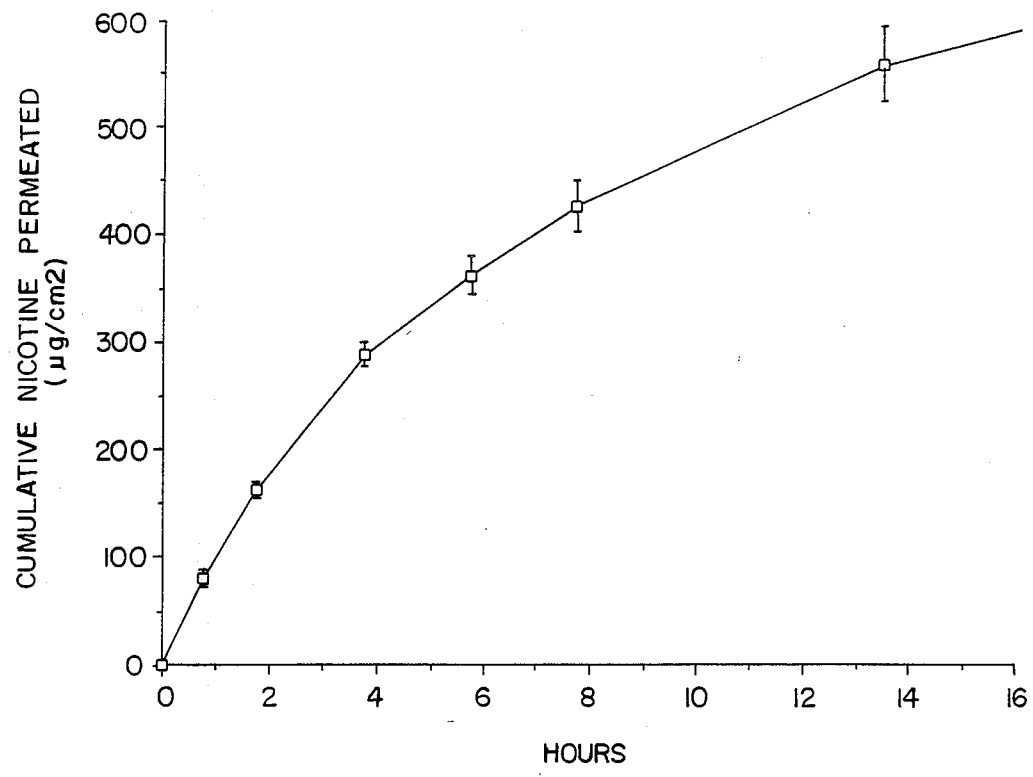
FIG. 3 shows the in vitro permeation of nicotine through human cadaver skin from a transdermal drug delivery device fabricated according to the presently disclosed method.

A bandage for delivering nicotine transdermally for approximately 16 hours was prepared as follows. The anchor adhesive was coated onto a facestock of about 0.0015" flexible polyester laminate at a coating weight of 6.5 mg/cm$^2$. The composition of the anchor adhesive was approximately 1:5:2 polyisobutylene, m.w. 1.2 $\times 10^6$/ polyisobutylene, m.w. 35,000/ polybutene blend, m.w. 2300. The pressure-sensitive sensitive contact adhesive having the same composition as the anchor adhesive layer was coated, also at 6.5 mg/cm$^2$, onto a 0.003" siliconized polyester release liner. The source layer, a 100% non-woven polyester fabric at 4.2 mg/cm$^2$, was then laminated to the anchor adhesive. Nicotine free base was deposited, neat, onto the source layer using a fine mist airbrush in a uniform pattern, at about 0.9 mg/cm$^2$. The contact adhesive/release liner composite was then laminated onto the exposed surface of the drug reservoir, forming a laminate of the final device as shown in FIG. 1. Individual devices were die cut from the laminated product. The resulting in vitro skin permeation over 13 hours is shown in FIG. 3.

EXAMPLE 2

Example 1 was repeated, except that prior to deposition the nicotine was diluted with freon to a concentration of 10 wt. % to facilitate dispersal in the source layer. After deposition, the freon is removed by blowing warm air (about 30° C.) over the laminate for about 2 minutes.

EXAMPLE 3

A bandage for delivering nitroglycerine was made in a manner similar to that described in Example 1 for the nicotine bandage. The nitroglycerine was deposited onto the source layer as a 10% solution in ethanol using polyethylene glycol monolaurate (PGML) as carrier. The ethanol was allowed to evaporate and the final laminate was prepared as described in Example 1.

EXAMPLE 4

A transdermal device for delivering nicotine monoacetate transdermally for approximately 16 hours was prepared as follows. A first subassembly PIB adhesive was coated onto a facestock of a 12.5 micron flexible polyester film at a coating weight of 4.0 mg/cm$^2$. The PIB adhesive was coated, also at 4.0 mg/cm$^2$, onto a 0.003" siliconized polyester release liner to provide a second subassembly. A 100% polyester non-woven fabric at 35 g/yd$^2$ was then laminated to the PIB adhesive of the first assembly. Nicotine monoacetate was deposited, neat, onto the fabric in a uniform pattern, at about 1.1 mg/cm$^2$. The second subassembly composite was then laminated onto the exposed surface of the drug-containing fabric forming a five-layer laminate. Individual devices were die cut from the laminated composite.

What is claimed:

1. A method for making a transdermal delivery device, comprising:
    (a) laminating an adsorbent source layer to a pressure-sensitive, pharmaceutically acceptable contact adhesive layer, the contact adhesive layer comprised of a material that is permeable to the drug and which defines a basal surface for adhesion to skin;
    (b) printing a drug in liquid form onto the adsorbent fabric layer;
    (c) laminating an anchor adhesive layer to the source layer; and
    (d) applying a backing layer to the anchor adhesive layer which defines the upper surface of the device and is substantially impermeable to the drug.

2. The method of claim 1, further including (e) applying a release liner layer that covers the lower surface defined by the contact adhesive layer, the release liner adapted to be removed from the device prior to use to expose the lower surface of the contact adhesive layer.

3. The method of claim 1, wherein the drug is nicotine.

4. The method of claim 3, wherein the nicotine is in free base form.

5. The method of claim 3, wherein the nicotine is in salt form.

6. The method of claim 1, wherein the drug is nitroglycerin.

7. The method of claim 1, wherein the drug is fentanyl.

8. The method of claim 7, wherein the drug is fentanyl base.

9. The method of claim 7, wherein the drug is a pharmaceutically acceptable salt of fentanyl.

10. The method of claim 1, wherein said drug in liquid form is deposited on the source layer with a percutaneous absorption enhancer that increases the permeability of the skin to the drug.

11. A method for making a transdermal delivery device comprising:
    (a) laminating an adsorbent fabric layer to a pressure-sensitive, pharmaceutically acceptable contact adhesive layer, the contact adhesive layer comprised of a material that is permeable to the drug and which defines a basal surface for adhesion to skin;
    (b) printing an enhancer onto the adsorbent fabric layer;
    (c) laminating an anchor adhesive layer to the fabric layer; and
    (d) applying a backing layer to the anchor adhesive layer which defines the upper surface of the device and is substantially impermeable to the drug,
    wherein prior to said laminating, the drug is incorporated into the anchor adhesive layer, the contact adhesive layer, or both.

12. A method for making a fragrance-releasing device, comprising:
    (a) laminating an adsorbent fabric layer, adapted to initially retain a fragrance in liquid form, to a pressure-sensitive, pharmaceutically acceptable contact adhesive layer which defines a basal surface;
    (b) printing a fragrance in liquid form onto the adsorbent fabric layer, whereby the fragrance is incorporated and initially retained therein;
    (c) laminating an anchor adhesive layer to the fabric layer, the anchor adhesive layer comprised of a material that is substantially pormeable to the fragrance; and
    (d) applying a backing layer to the anchor adhesive layer which defines the upper surface of the device and is substantially permeable to the fragrance.

* * * * *